United States Patent
Carroll

(10) Patent No.: US 10,245,236 B1
(45) Date of Patent: Apr. 2, 2019

(54) METHOD AND PRODUCT FOR TREATING MOUTH-RELATED DISORDERS

(71) Applicant: Lisa Carroll, Broken Arrow, OK (US)

(72) Inventor: Lisa Carroll, Broken Arrow, OK (US)

( * ) Notice: Subject to any disclaimer, the term of this patent is extended or adjusted under 35 U.S.C. 154(b) by 0 days.

(21) Appl. No.: 15/869,199

(22) Filed: Jan. 12, 2018

(51) Int. Cl.
| | |
|---|---|
| *A61K 31/047* | (2006.01) |
| *A61P 1/00* | (2006.01) |
| *A23L 33/15* | (2016.01) |
| *A61K 9/00* | (2006.01) |
| *A23L 33/17* | (2016.01) |
| *A23L 33/00* | (2016.01) |
| *A23L 33/125* | (2016.01) |
| *A23L 33/175* | (2016.01) |

(52) U.S. Cl.
CPC .......... *A61K 31/047* (2013.01); *A23L 33/125* (2016.08); *A23L 33/15* (2016.08); *A23L 33/17* (2016.08); *A23L 33/175* (2016.08); *A23L 33/30* (2016.08); *A23L 33/40* (2016.08); *A61K 9/0053* (2013.01); *A61P 1/00* (2018.01); *A23V 2002/00* (2013.01)

(58) Field of Classification Search
CPC combination set(s) only.
See application file for complete search history.

(56) References Cited

U.S. PATENT DOCUMENTS

| | | | |
|---|---|---|---|
| 5,438,075 A | 8/1995 | Skubitz et al. | |
| 6,258,384 B1 * | 7/2001 | Stanley | A23G 9/366 424/600 |
| 2015/0320701 A1 * | 11/2015 | Shigeki | A61K 31/047 424/52 |
| 2016/0317600 A1 * | 11/2016 | Johns | A61K 31/202 |

OTHER PUBLICATIONS

Anderson et al., "Oral Glutamine Reduces the Duration and Severity of Stomatitis after Cytotoxic Cancer Chemotherapy," Cancer Oct. 1, 1998;83(7):1433-9.
Peterson et al., "Randomized, Placebo-Controlled Trial of Saforis for Prevention and Treatment of Oral Mucositis in Breast Cancer Patients Receiving Anthracycline-Based Chemotherapy," Cancer Jan. 15, 2007;109(2):322-31.

* cited by examiner

*Primary Examiner* — Savitha M Rao
(74) *Attorney, Agent, or Firm* — Andrew S. Langsam; Pryor Cashman LLP

(57) ABSTRACT

A treatment product for a mouth-related disorder, and associated method of treatment, where the treatment product includes an initially sealed dispensing package and a composition disposed in said package, the composition including one or more vitamins, one or more amino acids, and Xylitol (a natural composition), where the composition is a liquid at room temperature and solid or substantially solid when administered to a subject's mouth.

16 Claims, No Drawings

METHOD AND PRODUCT FOR TREATING MOUTH-RELATED DISORDERS

TECHNICAL FIELD

The present invention involves a method and new product for treating mouth-related disorders, including canker sores, orthodontic-associated pain, mucositis, and the like, through use of a specially-designed freezer pop.

BACKGROUND OF THE INVENTION

Mouth sores and associated oral-related pain are difficult to address in terms of efficient and expeditious treatment. In light of the moist environment of the human mouth, sores are not capable of drying out nor scabbing as part of the more normal surface healing process. As a result, sensitive nerve endings are exposed to friction, foods, and beverages, which can affect the healing process in a negative manner if the food or beverage is acidic, rough, caustic, "hot" in the spicy sense, etc. One example of a mouth sore is a canker sore, which is a small ulcer that may appear in different parts on the inside surface of the mouth. Canker sores are often uncomfortable and can make speaking and eating unpleasant and irritating. Additionally, canker sores can take up to two weeks to fully heal. Current treatment mechanisms involve drug-based topical application, including the use of corticosteroids and pain-relieving (analgesic) gels. However, these options merely address canker sore pain and inflammation and are often only mildly effective. Another prior option, Amlexanox (APHTHASOL), has since been discontinued for use in the United States. Moreover, many who suffer such canker sores desire to treat the same without using additional drugs, as they often don't want foreign chemical compositions in their body even if they are not already taking other drugs. Therefore, there is a need for a simple, drug-free treatment mechanism that works to not only externally treat a mouth sore but also internally treat the sore to improve the healing process and promote overall mouth health.

SUMMARY OF THE INVENTION

In general, in one aspect, the invention features a treatment product for a mouth-related disorder, including an initially sealed dispensing package and a composition disposed in said package, the composition including one or more vitamins, one or more amino acids, and Xylitol (a natural composition), where the composition is a liquid at room temperature and solid or substantially solid when administered to a subject's mouth.

Implementations of the invention may include one or more of the following features. The package may be a plastic sleeve. The one or more vitamins may be one or more of vitamin C in the form of ESTER-C vitamin C formula and vitamin B6 in the form of Pyridoxine HCL USP. The one or more amino acids may be one or more of L-Glutamine and L-Lysine HCL. The composition may further include a flavoring, two grams of protein, and/or Oral Syrup SF. The mouth-related disorder may be a canker sore, an orthodontic-associated pain or sore, or mucositis. The composition may provide a primary treatment in cool form to the mouth and a secondary treatment when ingested.

In general, in another aspect, the invention features a method for treating a mouth-related disorder, including administering, to a subject's mouth, a treatment product for a sufficient duration and under sufficient conditions effective to treat the subject, where the treatment product includes a package and a composition disposed in said package, the composition including one or more vitamins, one or more amino acids, and Xylitol (a natural composition), where the composition is a liquid at room temperature, where the sufficient duration is of such a duration that the treatment product reduces a clinical sign or symptom of the mouth-related disorder, and where the sufficient conditions are such that the composition is solid or substantially solid when administered to the subject's mouth.

Implementations of the invention may include one or more of the following features. The package may be an initially sealed plastic sleeve capable of collapsing as an ice pop. The one or more vitamins may be one or more of vitamin C in the form of ESTER-C vitamin C formula and vitamin B6 in the form of Pyridoxine HCL USP. The one or more amino acids may be one or more of L-Glutamine and L-Lysine HCL. The composition may further include a flavoring, two grams of protein, and/or Oral Syrup SF. The mouth-related disorder may be a canker sore, an orthodontic-associated pain or sore, or mucositis. The composition may provide a first therapeutic benefit to the mouth upon direct application and a second therapeutic benefit when ingested.

DETAILED DESCRIPTION OF THE PREFERRED EMBODIMENTS

The present invention is directed to a method of treating mouth-related disorders, including canker sores, orthodontic-associated pain, mucositis, and the like, through use of a specially-designed freezer pop. The present invention is also directed to said specially-designed freezer pop.

The freezer pop of the present invention includes at least three components, namely vitamin(s), amino acid(s), and Xylitol, to assist in the external and internal treatment of mouth-related disorders. The one or more vitamins are selected for the purpose of improving body function and/or preventing or remedying disease. In a preferred embodiment, one or more of the following vitamins are included in the freezer pop of the present invention: vitamin C and vitamin B6. In a more preferred embodiment, vitamin C is selected as one of the one or more vitamins included in the freezer pop. Vitamin C is preferably included in the form of calcium ascorbate, such as but not limited to the form of the ESTER-C vitamin C formula. Vitamin B6 is preferably included in the form of Pyridoxine HCL USP. The one or more amino acids are selected for the purpose of healing wounds and/or repairing tissue. In a preferred embodiment, one or more of the following amino acids are included in the freezer pop of the present invention: L-Glutamine and L-Lysine HCL. Finally, the freezer pop includes Xylitol, a naturally-occurring carbohydrate (polyol) having a 5-carbon structure. Xylitol has been shown to interfere with bacteria's ability to adhere to tissue and teeth. This should be quite effective in treating the mouth sore. Moreover, Xylitol reduces bacteria's ability to produce biofilm, which makes bacteria more susceptible to antibiotic and natural immune system defenses. Xylitol may also serve as a natural sweetener in the present invention. Additionally, the freezer pop of the present invention may include flavorings to flavor the freezer pop, such as a strawberry flavoring, a grape flavoring, an orange flavoring, and the like. The freezer pop may also include an appropriate amount of protein (e.g., 2 grams of protein). Finally, the freezer pop may also include Oral Syrup SF, a sugar-free flavored syrup vehicle.

The freezer pop of the present invention is preferably a liquid at room temperature and a solid when subjected to adequately cold conditions, such as being placed in a freezer for a sufficient amount of time. The freezer pop is preferably packaged in a closed and sealed plastic sleeve, and therefore does not require freezer-refrigeration when being transported or stored, i.e., can remain in liquid form. In a preferred embodiment, the sleeve is approximately 5 inches long and approximately 1 inch wide. It may form, in cross section, an oval or circular shape. When ready for consumption, one end of the sleeve is cut off, thus exposing the end of the freezer pop. It is preferably longer than wide so as to be easily held and pushed up from the bottom, exposing more of it as it is consumed. In a preferred embodiment, the freezer pop is administered for treatment in solid or sufficiently solid, e.g., slush form. Once the freezer pop has reached solid or sufficiently solid state, a portion of the sleeve may be torn or cut to permit the freezer pop contents to be pushed up from the bottom and out of the sleeve and contact a user's mouth directly for administration. As the freezer pop is administered, the freezer pop first soothes the sore in the mouth, due to the coolness of the pop and the composition will immediately impact the sore. As the contents are subsequently digested by the user, the composition will be ingested and absorbed in the linings of the organs, especially the stomach, which will also provide advantage to treating the oral-based sore.

In a preferred embodiment, the mouth-related disorder to be treated is a canker sore (aphthous ulceration), such as recurrent aphthous stomatitis (RAS). In another embodiment, the mouth-related disorder to be treated is an orthodontic-associated pain or sore, such as those caused by braces or dentures. In another embodiment, the mouth-related disorder to be treated is mucositis, such as radiation or chemotherapy-induced mucositis. The freezer pop of the present invention may also be administered to persons suffering from sore throats, cold sores (e.g., herpes simplex virus type 1), mouth sores resulting from tobacco cessation, and nutritional deficiencies (e.g., vegan diet), or recovering from oral surgery (e.g., tonsillectomy). In an alternate form of the invention, the freezer pop may be in the form of a lozenge, which can be placed in the mouth and administered in a similar fashion as to sucking on an ice cube. That, too, will be beneficial.

Benefits of administering the freezer pop of the present invention are two-fold—short term benefits and long term benefits. Short term benefits, e.g., instant benefits, include numbing and/or soothing effects directed to mouth pain and inflammation. This is a result of a cold/ice/slush quality of the freezer pop and the composition of the pop itself. Additionally, after several minutes of administering the freezer pop to a user's mouth, the lining of said mouth will develop a protective film akin to lotion applied to cracked hands. Long term benefits include benefits derived from digestion of the freezer pop. Specifically, nutrients disposed in the freezer pop are digested and processed to thereby promote accelerated healing of the mouth lining and reduce the duration of the mouth sore.

The embodiments and examples above are illustrative, and many variations can be introduced to them without departing from the spirit of the disclosure or from the scope of the invention. For example, elements and/or features of different illustrative and exemplary embodiments herein may be combined with each other and/or substituted with each other within the scope of this disclosure. Therefore, it is intended that the invention not be limited to the particular embodiments disclosed, but that the invention will include all embodiments falling within the scope of the claims.

What is claimed is:

1. A treatment product for a mouth-related disorder, comprising:
    an initially sealed dispensing package, and
    a composition disposed in said package, the composition comprising one or more vitamins, one or more amino acids, and Xylitol,
    wherein the composition is a liquid at room temperature and solid or substantially solid when first intended to be administered to a subject's mouth,
    wherein the one or more vitamins includes vitamin C in the form of ESTER-C vitamin C formula and vitamin B6 in the form of Pyridoxine HCL USP, and
    wherein the one or more amino acids includes L-Lysine HCL and L-Glutamine.

2. The treatment product of claim 1, wherein the package is a plastic sleeve.

3. The treatment product of claim 1, wherein the composition further comprises a flavoring.

4. The treatment product of claim 1, wherein the composition further comprises two grams of protein.

5. The treatment product of claim 1, wherein the composition further comprises a sugar free syrup vehicle.

6. The treatment product of claim 1, wherein the mouth-related disorder is one or more of a canker sore, an orthodontic-associated pain or sore, or mucositis.

7. The treatment product of claim 1, wherein said composition provides a primary treatment of said composition in cool form to the mouth and a secondary treatment of said composition when ingested.

8. A method for treating a mouth-related disorder, comprising:
    administering, to a subject's mouth, a treatment product for a sufficient duration and under sufficient conditions effective to treat the subject,
    wherein the treatment product comprises:
        a package; and
        a composition disposed in said package, the composition comprising one or more vitamins, one or more amino acids, and Xylitol,
        wherein the composition is a liquid at room temperature,
    wherein the sufficient duration is of such a duration that the treatment product reduces a clinical sign or symptom of the mouth-related disorder,
    wherein the sufficient conditions are such that the composition is solid or substantially solid when first intended to be administered to the subject's mouth,
    wherein the one or more vitamins includes vitamin C in the form of ESTER-C vitamin C formula and vitamin B6 in the form of Pyridoxine HCL USP, and
    wherein the one or more amino acids includes L-Lysine HCL and L-Glutamine.

9. The method of claim 8, wherein the package is an initially sealed plastic sleeve capable of collapsing as an ice pop.

10. The method of claim 8, wherein the composition further comprises a flavoring.

11. The method of claim 8, wherein the composition further comprises two grams of protein.

12. The method of claim 8, wherein the composition further comprises a sugar free syrup vehicle.

13. The method of claim 8, wherein the mouth-related disorder is a canker sore.

14. The method of claim 8, wherein the mouth-related disorder is an orthodontic-associated pain or sore.

15. The method of claim 8, wherein the mouth-related disorder is mucositis.

16. The method of claim 8, wherein said composition provides a first therapeutic benefit to the mouth upon direct application and a second therapeutic benefit when ingested.

* * * * *